United States Patent
Hatton et al.

(10) Patent No.: US 12,402,209 B2
(45) Date of Patent: Aug. 26, 2025

(54) VAPORIZATION DEVICE WITH LIP SENSING

(71) Applicant: Pax Labs, Inc., San Francisco, CA (US)

(72) Inventors: Nicholas J. Hatton, Oakland, CA (US); James Monsees, San Francisco, CA (US); Adam Bowen, San Mateo, CA (US)

(73) Assignee: PaxLabs, Inc., San Francisco, CA (US)

( * ) Notice: Subject to any disclaimer, the term of this patent is extended or adjusted under 35 U.S.C. 154(b) by 0 days.

(21) Appl. No.: 18/651,121

(22) Filed: Apr. 30, 2024

(65) Prior Publication Data

US 2024/0284562 A1    Aug. 22, 2024

Related U.S. Application Data

(63) Continuation of application No. 17/743,316, filed on May 12, 2022, now Pat. No. 12,004,269, which is a continuation of application No. 17/086,001, filed on Oct. 30, 2020, now Pat. No. 11,388,781, which is a continuation of application No. 16/512,791, filed on Jul. 16, 2019, now Pat. No. 10,849,366, which is a continuation of application No. 15/456,297, filed on Mar. 10, 2017, now Pat. No. 10,405,582.

(60) Provisional application No. 62/306,616, filed on Mar. 10, 2016.

(51) Int. Cl.
*H05B 1/02* (2006.01)
*A24F 40/50* (2020.01)
*A24F 40/51* (2020.01)

(52) U.S. Cl.
CPC .......... *H05B 1/0244* (2013.01); *A24F 40/50* (2020.01); *A24F 40/51* (2020.01); *H05B 2203/021* (2013.01)

(58) Field of Classification Search
None
See application file for complete search history.

(56) References Cited

U.S. PATENT DOCUMENTS 10,201,186 B2 * 2/2019 Alarcon ............... H05B 1/0252
10,506,829 B2 * 12/2019 Freelander ............. A24F 40/30

* cited by examiner

*Primary Examiner* — Ross N Gushi
(74) *Attorney, Agent, or Firm* — FisherBroyles, LLP

(57) ABSTRACT

Apparatuses, including systems and devices ("vaporizers"), for vaporizing material to form an inhalable aerosol that include capacitive lips sensing to regulate the temperature of the vaporizer, including transiently boosting the temperature. Methods of operating a vaporizer having a capacitive lip sensor are also described.

18 Claims, 13 Drawing Sheets

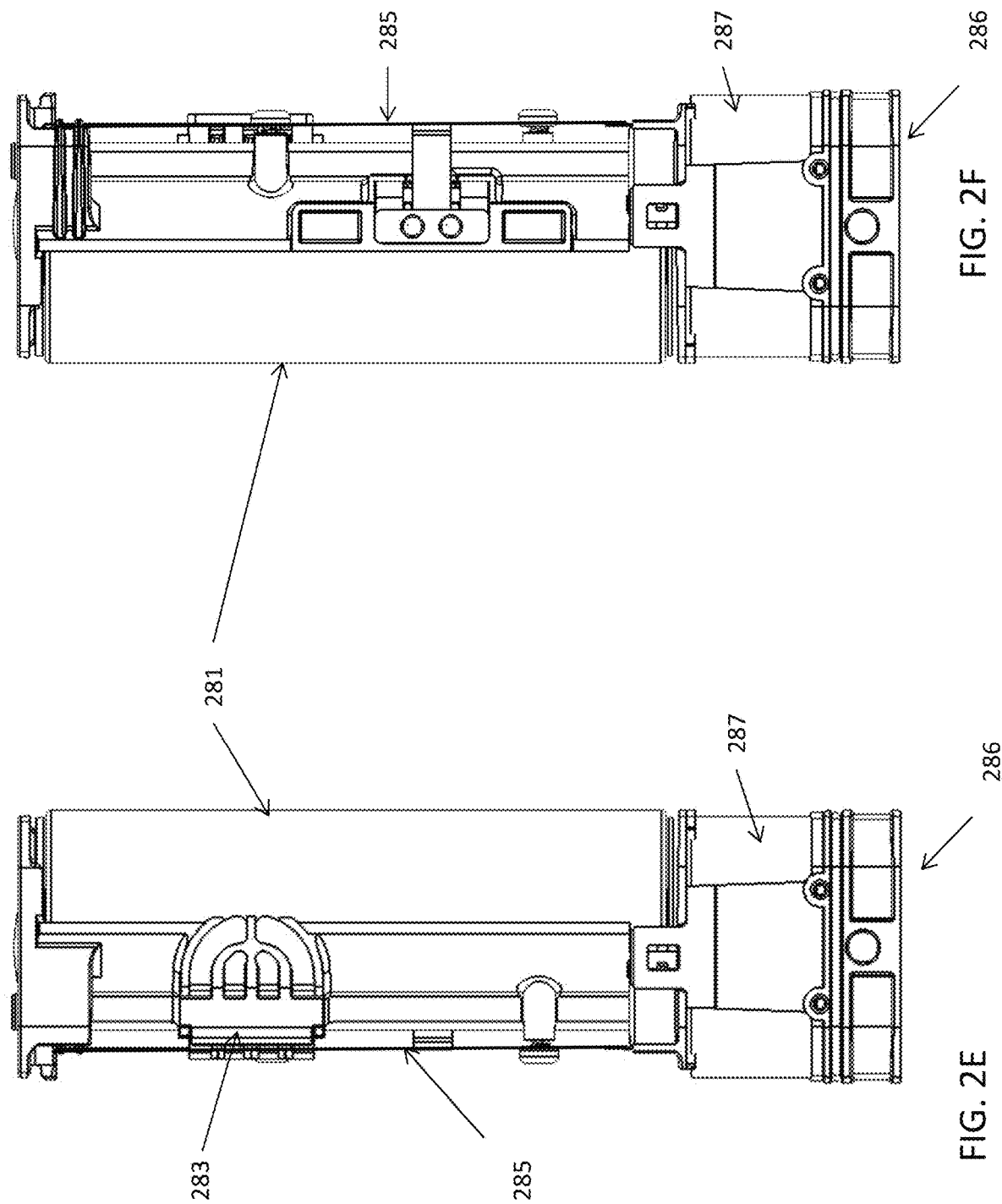

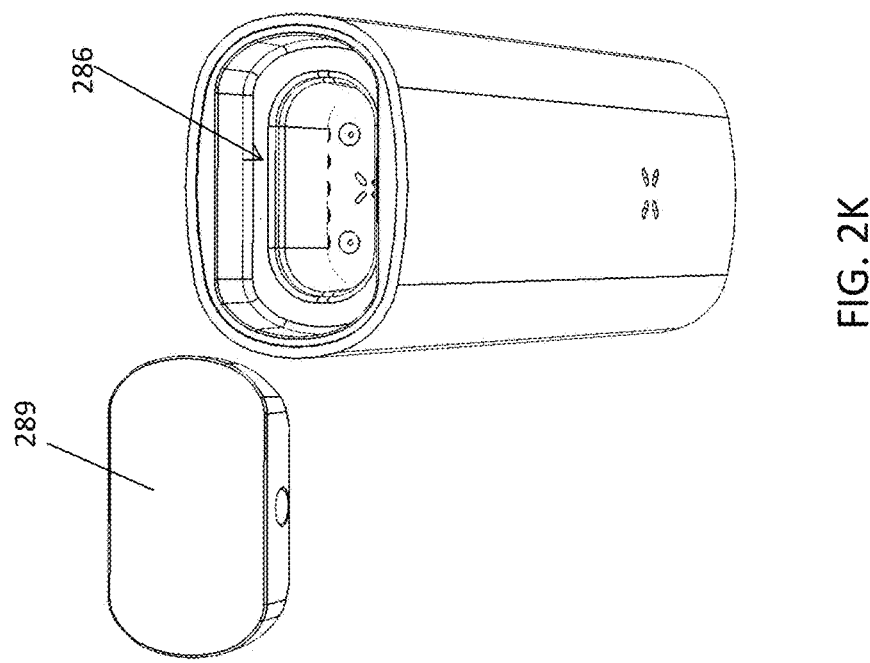
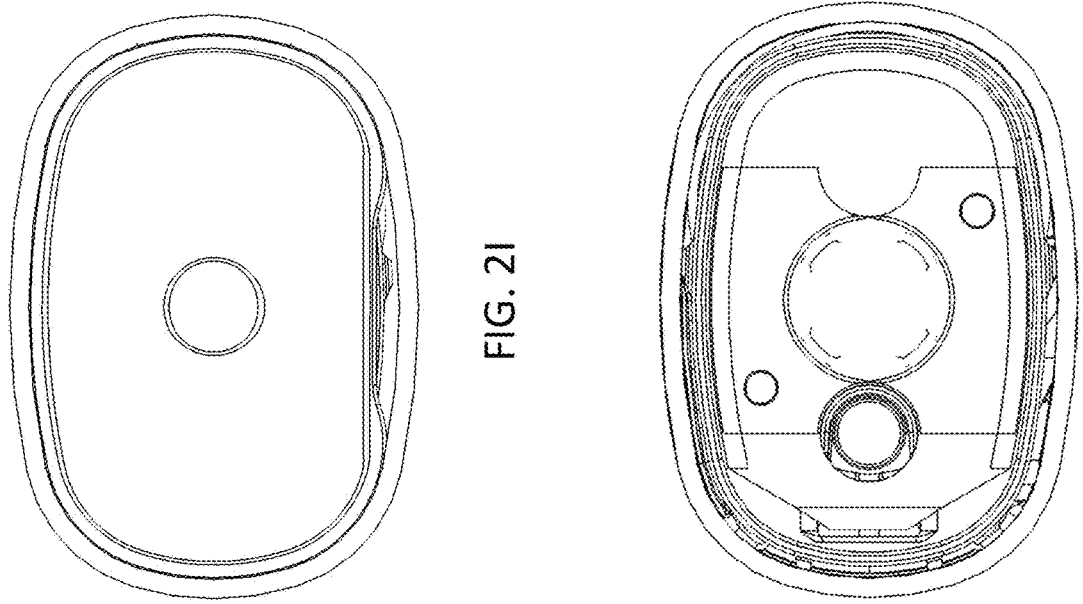

VAPORIZATION DEVICE WITH LIP SENSING

CROSS REFERENCE TO RELATED APPLICATIONS

This application is a continuation of U.S. patent application Ser. No. 17/743,316, filed May 12, 2022, entitled "VAPORIZATION DEVICE WITH LIP SENSING," which is a continuation of U.S. patent application Ser. No. 17/086,001, filed Oct. 30, 2020, now U.S. Pat. No. 11,388,781, entitled "VAPORIZATION DEVICE," which is a continuation of U.S. patent application Ser. No. 16/512,791, filed Jul. 16, 2019, now U.S. Pat. No. 10,849,366, entitled "VAPORIZATION DEVICE WITH LIP SENSING," which is a continuation of U.S. patent application Ser. No. 15/456,297, filed Mar. 10, 2027, now U.S. Pat. No. 10,405,582, entitled "VAPORIZATION DEVICE WITH LIP SENSING," which claims priority to U.S. Provisional Application No. 62/306,616, filed Mar. 10, 2016, entitled VAPORIZATION DEVICE WITH LIP SENSING". The entire contents of these applications are incorporated herein by reference in their entirety.

This application may be related to: U.S. patent application Ser. No. 15/261,823, titled "LOW TEMPERATURE ELECTRONIC VAPORIZATION DEVICE AND METHODS," filed on Sep. 9, 2016, Publication No. US-2016-0374400-A1; which is a continuation of U.S. patent application Ser. No. 13/587,416, titled "LOW TEMPERATURE ELECTRONIC VAPORIZATION DEVICE AND METHODS," filed on Aug. 16, 2012, now U.S. Pat. No. 9,408,416; U.S. patent application Ser. No. 13/837,438, titled "LOW TEMPERATURE ELECTRONIC VAPORIZATION DEVICE AND METHODS," filed on Mar. 15, 2013, Publication No. US-2013-0312742-A1; U.S. patent application Ser. No. 14/581,666, titled "VAPORIZATION DEVICE SYSTEMS AND METHODS," filed on Dec. 23, 2014, Publication No. US-2015-0208729-A1; and U.S. patent application Ser. No. 15/379,898, titled "VAPORIZATION DEVICE SYSTEMS AND METHODS," filed on Dec. 15, 2016; which is a continuation of U.S. patent application Ser. No. 15/053,927, titled "VAPORIZATION DEVICE SYSTEMS AND METHODS," filed on Feb. 25, 2016, now U.S. Pat. No. 9,549,573. Each of these patents and patent application are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Vaporizers are increasingly popular devices that are used to vaporize the active ingredients of a material, such as a plant material, for inhalation by a user. The vapor is typically released by a heating element that heats the vaporizable material through convection or conduction. Typically, the user activates the vaporizer by taking a puff or pressing a button. Many of the vaporizers today are small, hand-held, and battery-powered for case of use.

There are several disadvantages associated with current battery-powered vaporizers. One disadvantage is that the battery life can be low due to constant heating of the device. Another disadvantage is that the temperature of the oven can vary, particularly when ambient air is drawn therethrough, which can make consistent heating and vaporizing of the material difficult.

Described herein are apparatuses and methods that may address the issues discussed above.

SUMMARY OF THE DISCLOSURE

The present invention relates generally to apparatuses, including systems and devices, for vaporizing material to form an inhalable aerosol. Specifically, these apparatuses may include vaporizers. The vaporizer devices described herein may be similar to the vaporizer devices described, for example, in U.S. Patent Application Publication Nos. 2013-0042865, 2013-0312742, and 2015-0208729, herein incorporated by reference in their entirety. Such devices may include a capacitive touch (e.g., lip, hand, etc.) sensor that may be adapted to adjust the temperature of the heater during control of the apparatus. For example, an apparatus may be configured to adjust the heater to boost the temperature upon contact with a user's lip. This boost may transiently (e.g., for 0.5 sec, 1 sec, 2 sec, 3 sec, 4 sec, 5 sec, etc.) increase the temperature of the heater by a predetermined amount (e.g., 1° C., 2° C., 3° C., 4° C., 5° C., 6° C., 7° C., etc.) or percentage of a target (e.g., preset) temperature. This may help accommodate heating and cooling of the heater during draw (inhalation) on the device, and may enhance the user experience. The temperature boost may be achieved by increasing the duty cycle over which power is applied by the controller to the heater, e.g., increasing the duty cycle to 100 percent until the temperature reaches the target boost temperature (e.g., the pre-determined amount, such as 5° C., over a set temperature) or the transient boost period ends.

In addition, the capacitive sensors (e.g., capacitive lip sensors) described herein may be used to place the apparatus into a 'sleep' mode when no contact (e.g., lip sensing), and therefore no activity, is sensed after a predetermined period of time. For example, the capacitive sensing may be used to determined when no lip has been sensed (e.g. no increase in capacitance) for greater than an idle period (e.g., of 10 seconds, 15 seconds, 20 seconds, 25 seconds, 30 seconds, 40 seconds, 45 seconds, 1 min, etc.), and thereafter reduce the temperature of the heater by a predetermined initial reduction amount (e.g., 2, 3, 4, 5, 6, 10° C., etc.). If no new lip sensing (capacitance increase compared to a baseline) is detected for some continuing idle period (e.g., 10 seconds, 15 seconds, 20 seconds, 25 seconds, 30 seconds, 40 seconds, 45 seconds, 1 min, etc.) then the apparatus will again reduce the temperature by a predetermined step amount (e.g., 2, 3, 4, 5, 6, 10° C., etc.). This process may be continued through additional cycles as long as the no lip sensing is detected by the capacitance (lip) sensor, or the apparatus may shut the device off completely. In some variations, rather than cooling the heater in steps when the apparatus is inactive, the apparatus may instead begin a continuous cool-down period.

For example, a vaporizer device having capacitive lip sensing may include: a reservoir configured to hold a vaporizable material; a heater configured to heat the vaporizable material; a mouthpiece in communication with the reservoir; a capacitive lip sensor configured to output an instantaneous capacitance reading; and a controller (e.g., microcontroller) configured to: regulate a temperature of the heater to a preselected temperature; obtain the instantaneous capacitance reading from the capacitive lip sensor; determine a difference between the instantaneous capacitance reading and a baseline capacitance; and increase the temperature of the heater to an override temperature for a boost time period when the difference is above a threshold.

A vaporizer device may alternatively or additionally include: a reservoir configured to hold a vaporizable material; a heater configured to heat the vaporizable material; a mouthpiece in communication with the reservoir; a capacitive sensor (e.g., a capacitive lip sensor) configured to output an instantaneous capacitance reading; and a controller configured to: regulate a temperature of the heater to a first temperature; obtain sensor readings from the capacitive sensor; determine a difference between the instantaneous capacitance reading and a baseline capacitance; and reduce the temperature of the heater to a second temperature that is lower than the first temperature when the difference is below a threshold for a predetermined period of time.

A vaporizer device may include: a reservoir configured to hold a vaporizable material; a heater configured to heat the vaporizable material; a mouthpiece in communication with the reservoir; a capacitive lip sensor configured to detect a capacitance proximate to the mouthpiece; and a controller configured to regulate a temperature of the heater to a predetermined temperature, to determine the presence of a user's lip based upon a change in capacitance detected by the capacitive lip sensor, and to transiently boost the temperature of the heater when a lip is detected.

In any of these apparatuses described herein, the capacitive sensor (e.g., capacitive lip sensor) may be positioned on, near, within or behind the mouthpiece, e.g., proximate to the mouthpiece. In some variations, the capacitive sensor may be a conductor (e.g., a conductive plate or fill) that is positioned behind the mouthpiece. Behind the mouthpiece may be between the mouthpiece, which may be removable, and the body of the apparatus. The body may be an elongate body (e.g., cylindrical body, etc.), e.g., between the mouthpiece and the controller, battery, etc. For example, the capacitive sensor may be a copper fill region of a circuit (e.g., flex circuit) that is positioned under and/or behind the mouthpiece to detect contact between the mouthpiece (which may be any appropriate material, including a silicone mouthpiece) and the user's lips or other body part (e.g., fingers, etc.). In some variations, the capacitive sensor may comprise a flex circuit onto which a conductive region has been layered.

In general, the reservoir may be an oven, and the heater may be in thermal contact with the oven, and/or integrated into the oven. The oven may be be configured to hold a solid (e.g., loose-leaf) material. The reservoir may be a tank, including a tank holding a liquid, gel, or semi-solid material that is configured to be vaporized (e.g., a tobacco solution, a *cannabis* solution, etc.). Any of the apparatuses described herein may include a wick or wicking mechanism for heating the vaporizable material, including drawing the vaporizable material into thermal contact with the heater, which may include a coil (e.g., resistive coil). Alternatively or additionally, the heater may be in thermal (conductive, convective and/or radiant) contact with the reservoir. For example, the reservoir may be an oven that is directly and/or indirectly heated by the heater.

The controller may be a microcontroller and may be referred to as a heater controller. The controller may receive raw or processed input from the capacitance sensor (e.g., the controller may receive capacitance values or values based on the capacitance values, including averaged, scaled, filtered, etc. capacitance values.

In some variations the controller determines, based on the instantaneous capacitance readings received from the capacitance sensor, the baseline values. For example, the controller may be configured to determining the baseline based on the instantaneous sensor readings by taking a running average of the instantaneous sensor readings. The baseline may be frozen or held at a value (e.g., prior baseline value) once the sensor determines that a large change in capacitance has been detected (e.g., due to lip/skin contact or the like). For example, the controller may be configured to determine the baseline based on the instantaneous capacitance readings and may be configured to hold the baseline at a prior value of the baseline while the instantaneous capacitance readings are above the baseline by a first offset value or below the baseline by a second offset value. The first offset value may be based on a percentage of the current baseline value (e.g., 0.5%, 1%, 1.5%, 2%, 2,5%, 3%, 4%, 5%, 6%, 7%, 8%, 9%, 10%, etc. of the baseline value). In this manner the apparatus may detect the sudden change "on" and "off" contact with the mouthpiece. Similarly, the second offset value may be zero, or it may be based on a percentage of the current baseline value (e.g., 0.5%, 1%, 1.5%, 2%, 2,5%, 3%, 4%, 5%, 6%, 7%, 8%, 9%, 10%, etc. of the baseline value). For example, the controller may be configured to hold the baseline at a prior value of the baseline while the instantaneous capacitance readings are above the baseline by a first offset value. In some variations the controller may be configured to hold the baseline at a prior value of the baseline while the instantaneous capacitance readings are above the baseline by a first offset value and further wherein the controller is configured to hold the baseline at the prior value of the baseline while the instantaneous capacitance readings are below the baseline by a second offset value.

The controller may be configured to determine the difference between the instantaneous capacitance reading and the baseline capacitance by determining a percent difference between the instantaneous capacitance and the baseline. The threshold of the controller may be greater than a 0.5% change (e.g., >about 1%, 1.5%, 2%, 2,5%, 3%, 4%, 5%, 6%, 7%, 8%, 9%, 10%, etc. of the baseline value) between the instantaneous capacitance and the baseline.

As mentioned above, the boost time period is between 2 and 5 seconds (e.g., approximately 3 seconds, etc.). The controller may be configured to increase the temperature of the heater by increasing the duty cycle of power applied to the heater for the boot time period. The controller may be configured to increase the temperature of the heater to the override temperature when the difference is greater than 0.5% above the baseline. The controller may be configured to increase the temperature of the heater to the override temperature when the difference is greater than x % (e.g., 0.5%, 1%, 2%, 5%, 10%, etc.) above the baseline.

BRIEF DESCRIPTION OF THE DRAWINGS

FIGS. 2E and 2F illustrate internal left and right views, respectively, of an exemplary vaporizer device including lip sensing, with an outer covering removed.

FIGS. 2I and 2J show an end view of the vaporization device of FIGS. 2E-2H.

FIG. 2I shows the end with a mouthpiece (shows as a flat mouthpiece as in FIG. 1A, but any other mouthpiece, including the protruding mouthpiece of FIG. 1B may be used).

FIG. 2K illustrates the opposite end, including the heater (oven) and cover, of a vaporization device such as the one shown in FIGS. 2E-2H.

DETAILED DESCRIPTION

A device for generating an inhalable aerosol is provided herein comprising: a mouthpiece, a body, an oven, an electronic heater within the oven to heat a vaporizable material to generate an inhalable aerosol, and a temperature regulator.

In some embodiments, the electronic heater comprises a polyimide thin film ("flex") printed heater circuit. In certain embodiments, the electronic heater includes a soldered thermistor element for controlling the temperature of the oven. In certain embodiments, the device comprises a PID (proportional integral derivative) control loop to control operating temperature of the device.

In certain embodiments, the device includes a sensor, such as an accelerometer or other motion-based sensor or a capacitive (touch or lip) sensor to detect if the heater is being moved or used and/or if the device is being loaded by the user puffing on the device. These sensors can be used to help control the oven temperature. In some embodiments, a capacitive sensor (or other sensor) can be used to override the PID control loop and increase the temperature beyond the set temperature. In some embodiments, the capacitive sensor (or other sensor) can be used to place the device in an automatic cool-down mode and/or shut the device off.

Figure 1A:
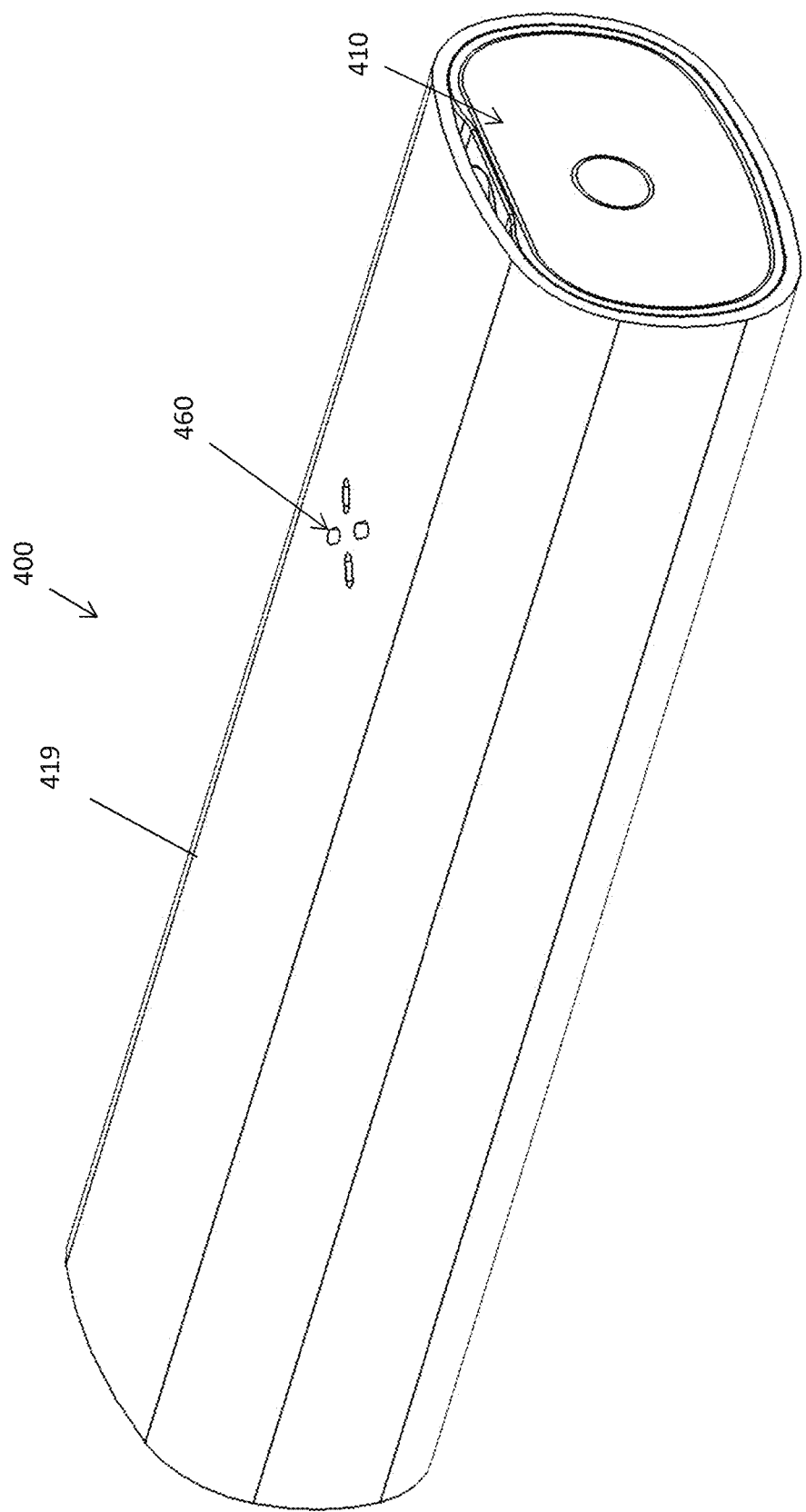
FIG. 1A shows one exemplary vaporizer device having a flat mouthpiece.
Figure 1B:
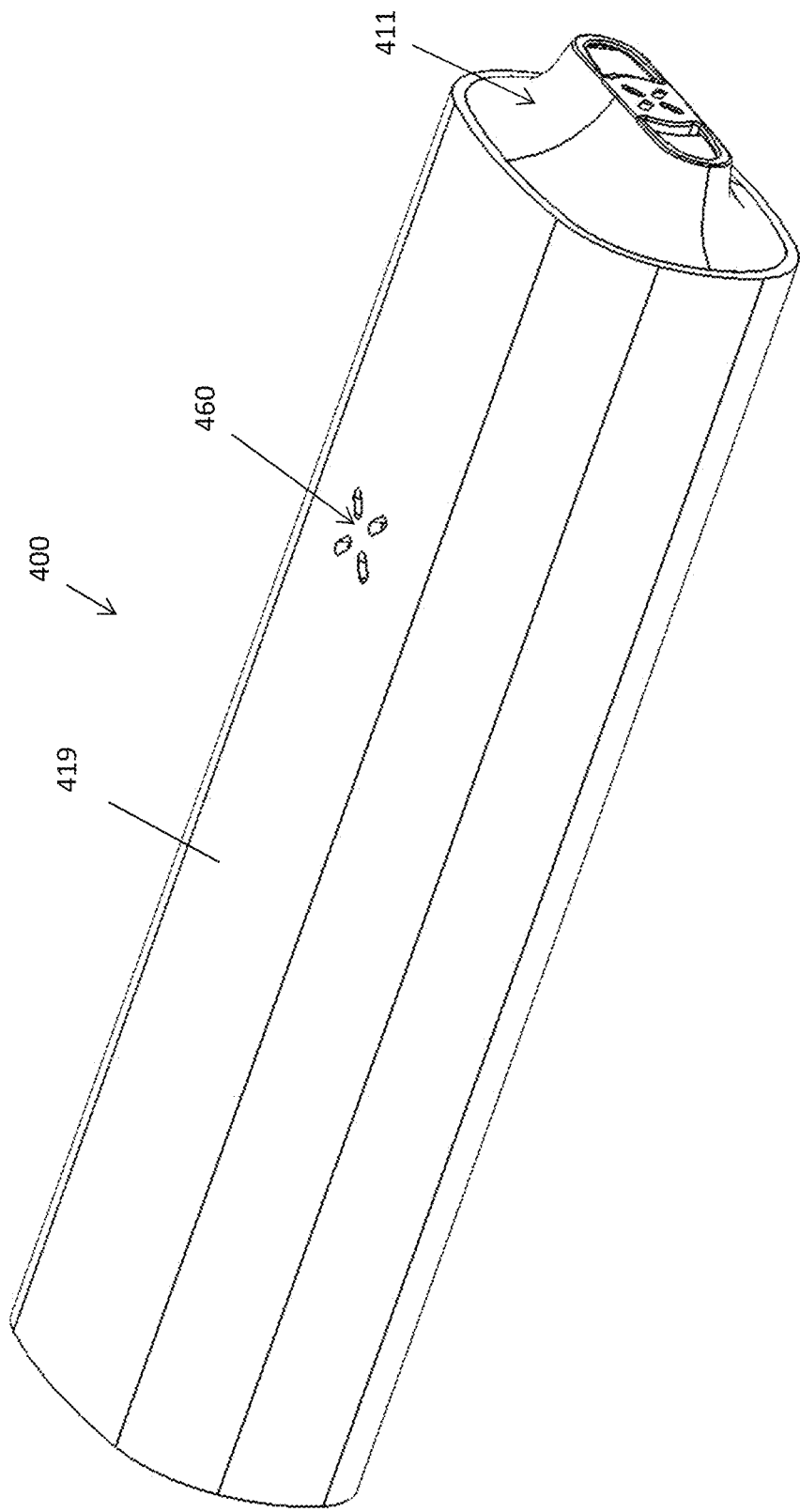
FIG. 1B shows a second exemplary vaporizer device having a protruding mouthpiece.
Figure 1C:
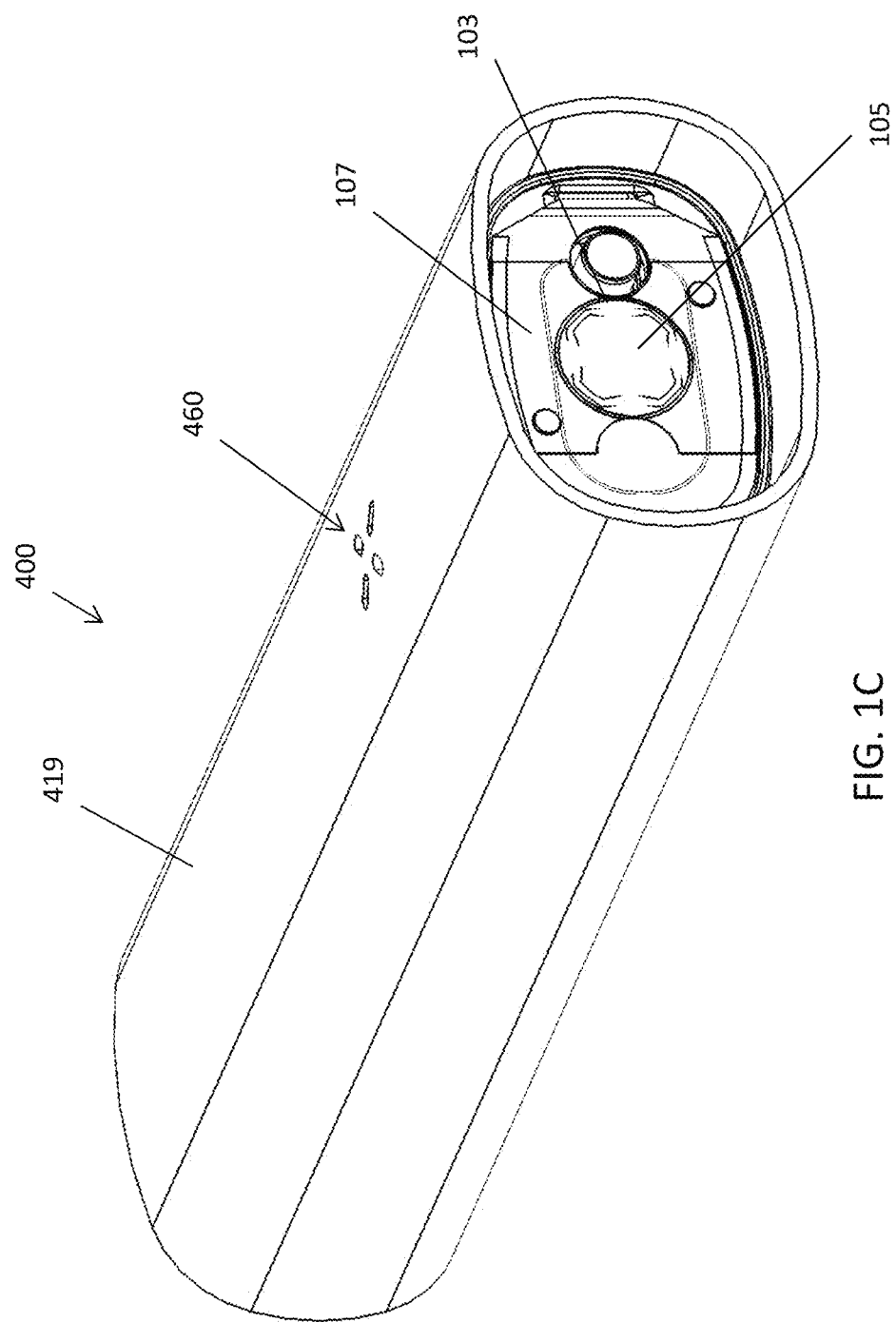
FIG. 1C shows the device of FIGS. 1A and 1B with the mouthpiece removed.

FIGS. 1A, 1B and 1C show variations of an exemplary device 400 with an outer body 419 and a mouthpiece 410. In FIG. 1A, the mouthpiece is a flat (e.g., silicone) mouthpiece having a side opening region through which the vapor may exit. In FIG. 1B the mouthpiece extends from the body of the vaporizer slightly, and includes an opening through which the vapor may exit. As will be described in greater detail below, the capacitive (lip) sensing described herein may operate equally as well with either mouthpiece. Further the mouthpiece may be made of any appropriate material, including both conductive and non-conductive materials. For example, the mouthpiece may be polymeric (e.g., silicone), plastic, metal, ceramic, etc.

The body 419 can be a single extruded aluminum outer body. Further, the mouthpiece 410 can be removable from the body 419. The device 400 further includes an indicator 460, such as an LED indicator. In some embodiments, the LED indicator 460 can indicate a temperature status and/or activation status of the device.

As shown in FIG. 1B, the device 400 can include a flexible circuit 107 configured to control operation of the device 400 (e.g., activation or deactivation of the device). Further, the device 400 can include a button 105 configured to turn the device on/off and/or cycle through temperature settings. In some embodiments, pressing the button 105 can cycle through the temperature settings (and, for example, the current temperature setting can be indicated by the LED indicator 460). The device 400 also includes a capacitive sensor 103 proximate to, i.e., just under, the mouthpiece 410. In one embodiment, the sensor 103 (capacitive lip sensor) can surround the on/off button 105 and can be positioned in a plane that is parallel to the mouthpiece 410. For example, the capacitive sensor 103 can be a copper pad that has a thickness and/or width, e.g., of between about ½ inches and 1 inch, such as about ¾ inches. Because the copper pad faces the lip when the lip is placed thereon, it can be geometrically tuned to be sensitive thereto. The capacitive sensor 103 can be configured to determine a change in capacitance thereacross (and thus the presence of a lip).

Figure 2A:
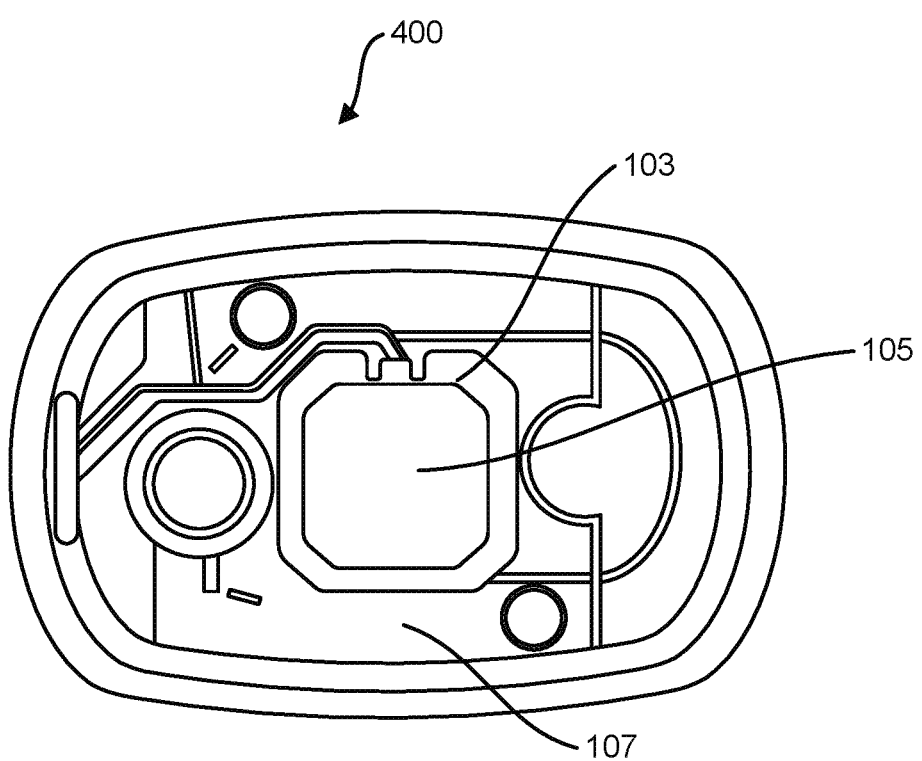
FIGS. 2A-2D show various views of the interior of the vaporizer device of FIGS. 1A-1C.

FIG. 2A and FIGS. 2I-2J, illustrate the proximal end of an exemplary device, with the mouthpiece removed (FIGS. 2A and 2J) and with the mouthpiece in place (FIG. 2I). In FIG. 2A, the region under or behind the mouthpiece (which may be removable/replaceable) includes a button 105 input that (along with accelerometers and other inputs) may be used to control the operation of the apparatus. The capacitive sensor 103 may be a conductive material, such as copper or other conductive materials, on a board such as a flex circuit. One or more additional circuit elements (filtering circuitry, memory, averaging circuitry, etc.) may be used to enhance the signal from the capacitive sensor. In some variations a separate capacitive trace near the periphery of the device (not shown) may be included and used to subtract signal to remove artifacts from holding the device. Such additional capacitive trace(s) may not be necessary, as shown in the example of FIG. 2A, where the capacitive sensor is centrally positioned relative to the mouthpiece sides.

Figure 2B:
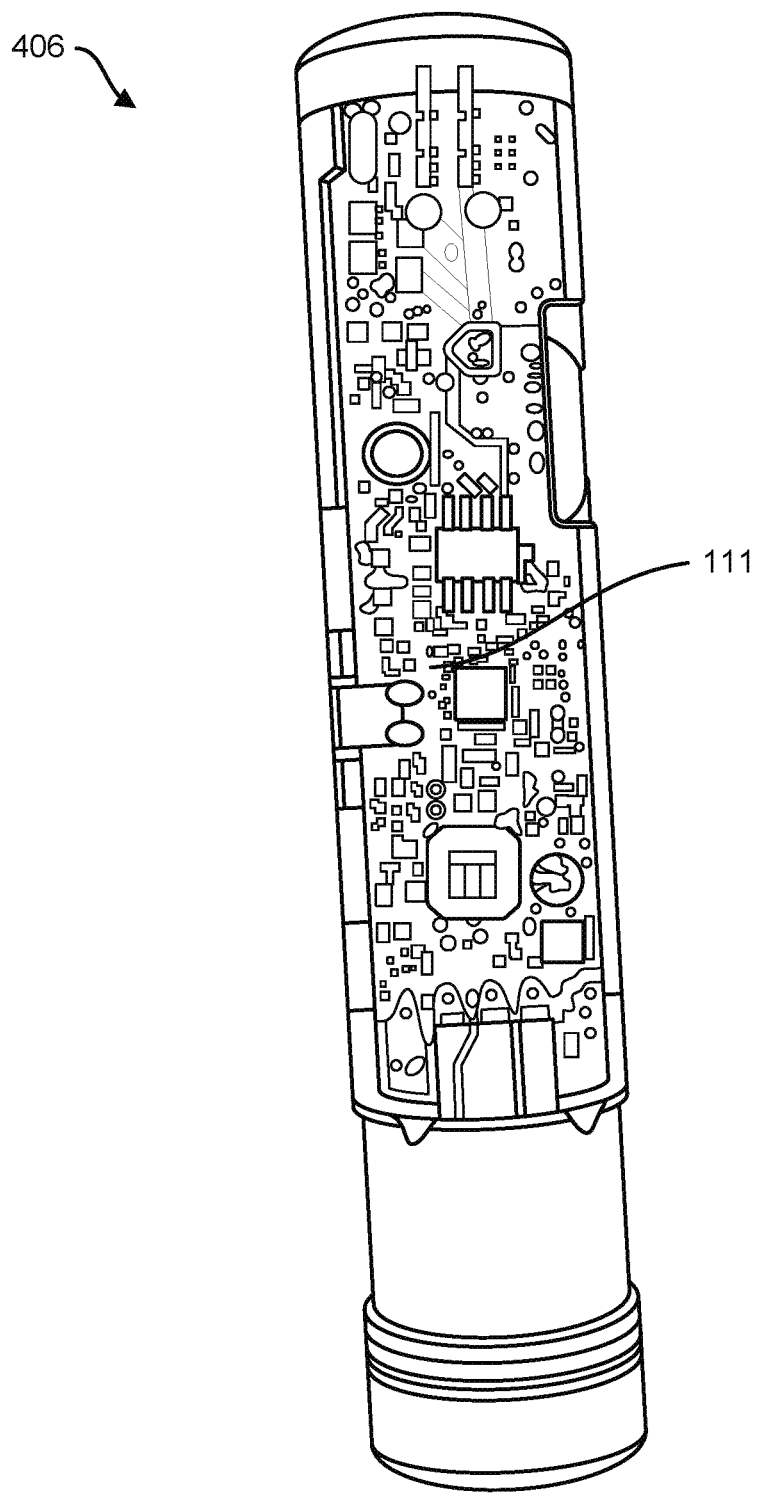
Figure 2C:
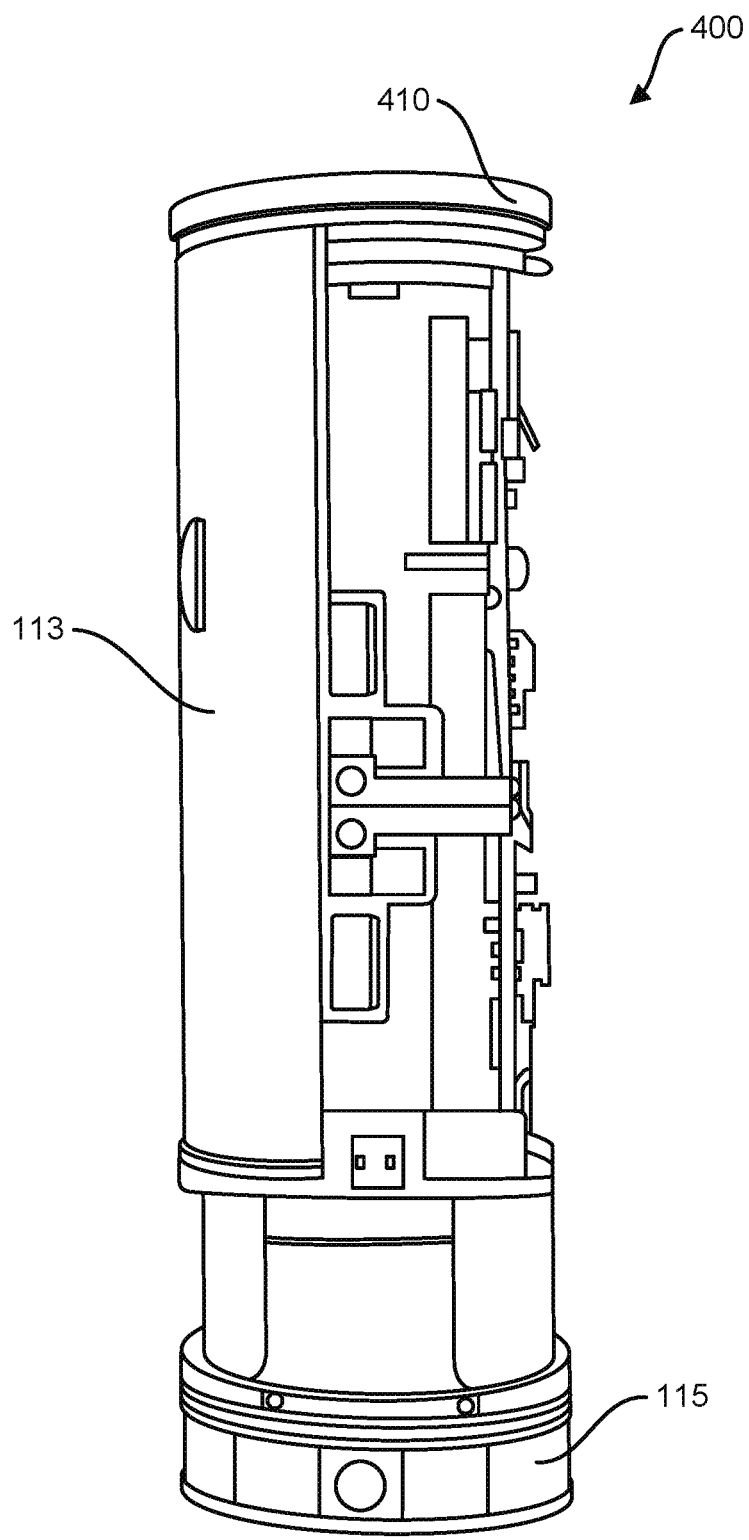
Figure 2D:
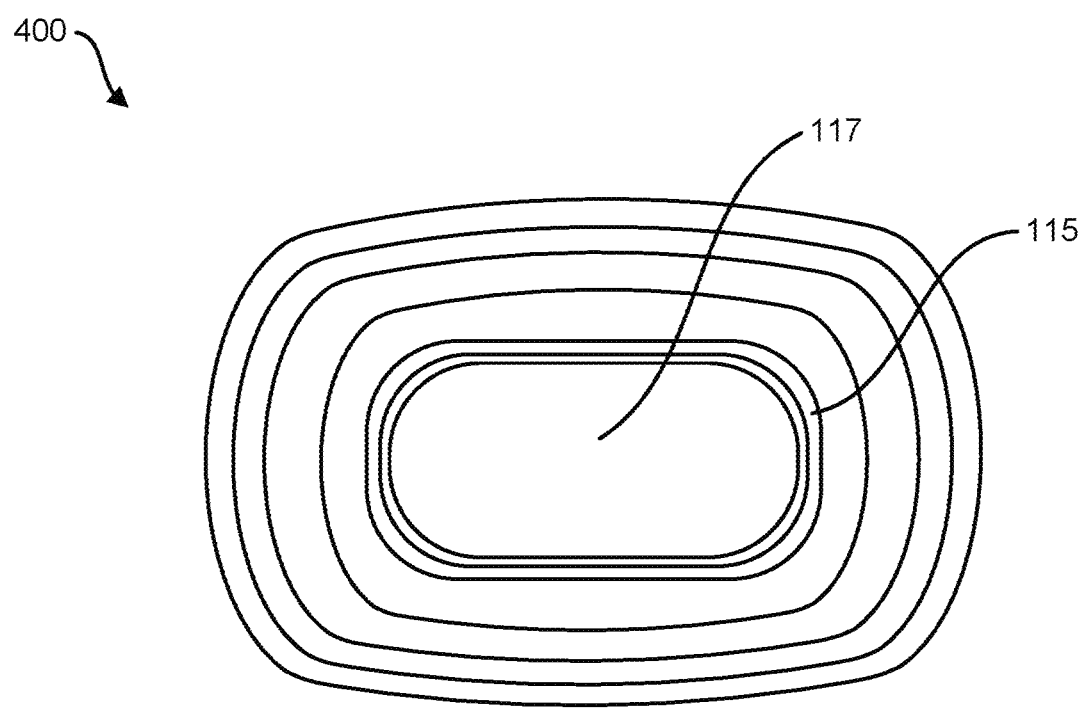

As is further shown in FIGS. 2B-2D, the device can include a circuit board 111 configured to control the device (such as the temperature of the device), a battery 113, an oven 115, and a heater 117 along a wall of the oven 115. In some embodiments, the device 400 includes aerogel insulation to maintain efficiency.

FIGS. 2E-2F illustrate front and back views, respectively, of an example of a vaporizer device in which the outer cover has been removed. In this example the devices include a battery 281, a controller (control circuitry on circuit board 285), an output (LEDs 283), and an oven to 286 to which a heater 287 is attached. The mouthpiece has been removed in this example, but would fit over the flex circuit connected to the controller (microcontroller) 285.

Figure 2H:
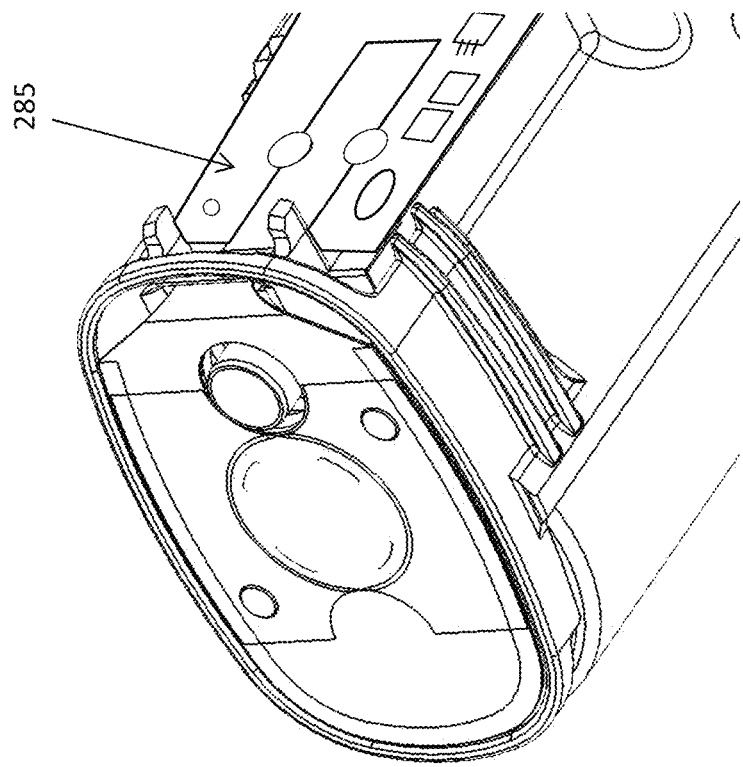
FIG. 2H shows the flex circuit and capacitive sensor of FIG. 2G in the context of a vaporization device with the mouthpiece and outer cover removed.
Figure 2G:
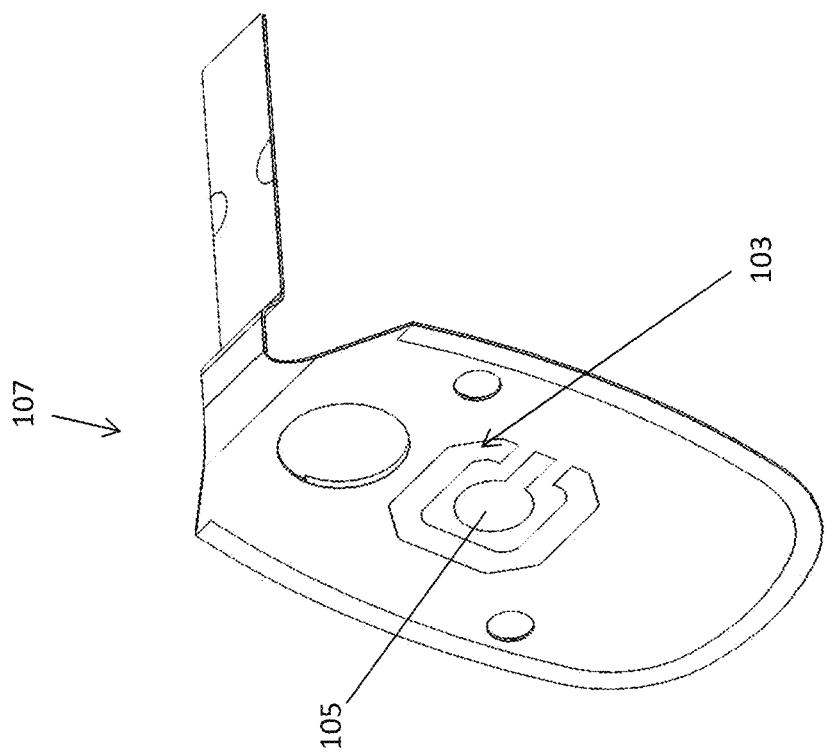
FIG. 2G shows a perspective view of a flex circuit including a capacitive (lip) sensor corresponding to the variation shown in FIGS. 2E and 2F.

FIGS. 2G and 2H illustrate one example of a capacitive sensor 103 on a flexible circuit. FIG. 2H shows the flex circuit 107 connected to the circuit board 285. The capacitive sensor in this example is a copper fill region (copper trace), though as discussed above, any appropriate conductor (or layer(s) of conductive/insulative materials) may be used.

FIG. 2K shows an example of the distal end of an apparatus having an oven 286 and a cover for the oven 289 that may be magnetically or otherwise attached.

Figure 3:
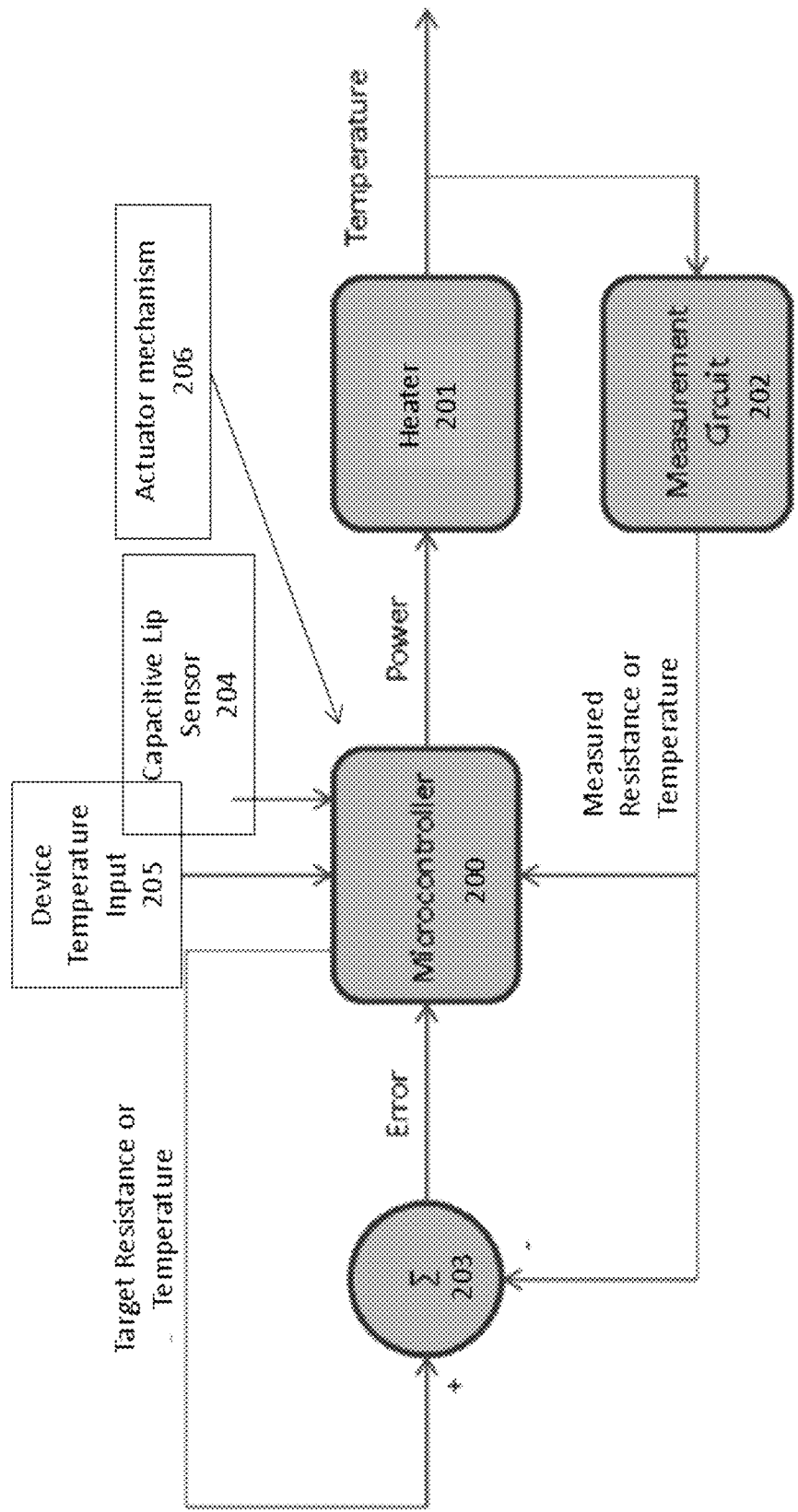
FIG. 3 shows an exemplary proportional integral derivative (PID) temperature control loop

As illustrated in the basic block diagram of FIG. 3, the device can utilize a PID control algorithm to control the temperature of the device. In general, the PID control algorithm calculates an "error" value as the difference between the measured temperature (or some value proportional to the temperature, such as the resistance) and the desired setpoint and uses that to control power to the heater. Thus, as shown in FIG. 3, the components used to control the PID algorithm can include a microcontroller 200, the device heater 201, the measurement circuit 203, a temperature input 205, a capacitive lip sensor 204, and an optional on/off activation mechanism 206. The microcontroller 200 can be used to run the PID control algorithm. Further, the microcontroller can control the amount of power provided to the heater 201 to thereby control the oven temperature. The measurement circuit 202 can include a measured temperature or measured value proportional to the temperature, such as resistance detected by a thermistor. The measured resistance or temperature can then be fed directly to the microcontroller 200 (such as to establish a baseline temperature or resistance) and/or can be fed to the summation block 203 for comparison computation of error relative to the desired temperature or resistance provided to the microcontroller 200 from temperature input 205. The microcontroller 200 can take set inputs regarding the temperature from the temperature input 205. This temperature input 205 be a user selected temperature or a preset temperature. The microcontroller 200 can also take input from a capacitive lip sensor 204, which will be described further below. Additional inputs from activation mechanism 206 can also be provided to the microcontroller, such as from an on/off button or a motion sensor (including when to activate or deactivate).

Figure 4:
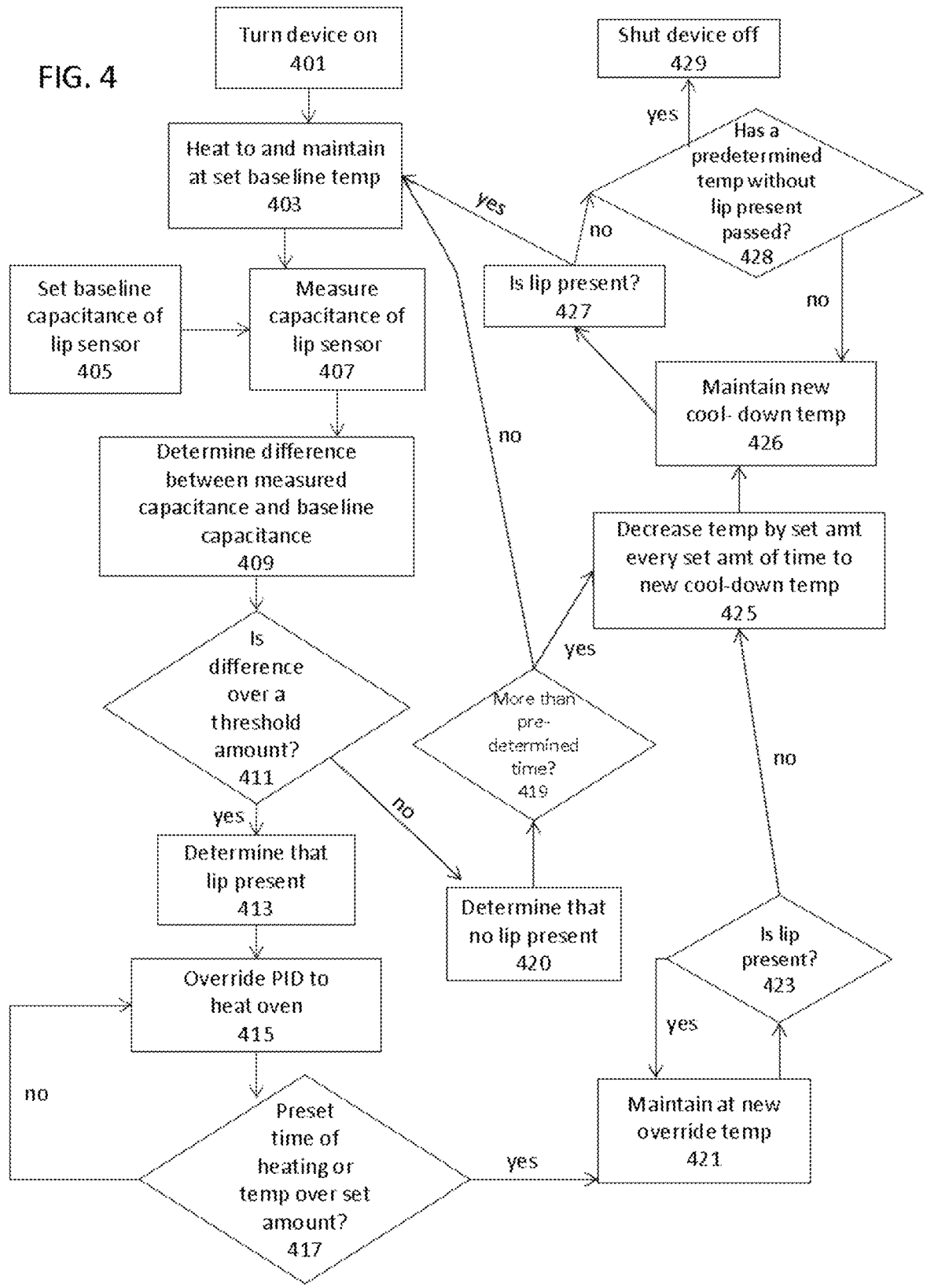
FIG. 4 shows a flow chart for boosting the temperature and/or lowering the temperature of a vaporizer device based upon readings from a capacitive lip sensor.

Referring to FIG. 4, in some embodiments, the input from the capacitive sensor can be used to increase the temperature of the device over the set temperature, decrease the temperature of the device over the set temperature, and/or turn the device off. As shown in FIG. 4, at step 401, the device is turned on. At step 403, the device oven is heated to, and maintained at, the set baseline temperature. The set baseline temperature can be user selected (such as from a plurality of different preselected temperatures, e.g., four preselected temperatures) or can be preprogrammed. The temperature can be, for example, between 190° C. and 240° C. In one embodiment, the user can select between a first temperature setting of between 190° C. and 205° C., a second temperature setting of between 205° C. and 220° C., a third temperature setting of between 220° C. and 230° C., and a fourth temperature setting of between 230° C. and 240° C. At step 405, a baseline capacitance of the lip sensor is determined. After the baseline capacitance has been determined and the device is heated to the set baseline temperature (and in some embodiments, even before the set baseline temperature has been reached), the capacitance of the lip sensor can be measured at step 407. The difference between the measured capacitance and the baseline capacitance can be determined at step 409. It can be determined whether that different is above a threshold amount at step 411. In one example, the threshold is an increase in capacitance of at least 0.5%-1%.

If the difference is above the threshold amount at step 411, then it can be determined that the lip is present at step 413 (and correspondingly, assumed that the user is puffing on and/or actively using the device). Thus, the PID (such as the PID control loop shown in FIG. 3) can be overridden at step 415 to actively heat the oven (for example, a 100% duty cycle can be activated). In some cases (e.g., where the device was already at the set baseline temperature), this step can heat the oven to a temperature above the set baseline temperature. In other embodiments, this step helps account for the cooling of the oven when air is drawn therethrough. It can then be determined whether a preset length of time (e.g., 3 seconds) or a preset amount (e.g., 5 degrees) over the baseline temperature has been reached at step 417. If not, then PID can continue to be overridden at step 415. If the preset length of time or the present amount over the baseline temperature has been reached at step 417, then the new override temperature can be maintained at step 421. At step 423, it can be detected whether a lip is present (e.g., using the steps outlined in steps 407, 409, 411, 413, and 420). If a lip is determined to be present at step 423, then the new override temperature can be maintained (step 421).

Referring back to step 411, if the difference in capacitance is not above the threshold amount, then it can be determined that no lip is present at step 420. At step 419, it can be determined whether no lip has been present for a predetermined amount of time (e.g., 3 minutes). If the predetermined amount of time has not been met, then the temperature can be maintained at the set baseline temperature (step 403).

If it has been more than the predetermined time (at step 419) or if the lip is not present (at step 423), then the device can enter an automatic cool-down mode at step 425. For example, in the auto-cool-down mode, the temperature can decrease by a set amount (e.g., 5 degrees) every set amount of time (e.g., 20 seconds) until a predetermined amount of time has passed (e.g., 1 minute). The new cool-down temperature can then be maintained at step 426. It can then be determined at step 427 whether a lip is present (e.g., using the steps outlined in steps 407m 409, 411, 413, and 420). If a lip is detected, then the heater can be returned to the set baseline temperature at step 403. If a lip is not detected, it can be determined whether a predetermined amount of time (e.g., 3 minutes) without presence of the lip has been met. If not, the new cool-down temperature can continue to be maintained at step 426. If the predetermined time without sensing a lip (e.g., 3 minutes) has passed, the device can shut off at step 429.

In some embodiments, the capacitive sensor can be used to turn the device on. In some embodiments, the capacitive sensor can be used to put the device in a lower temperature standby-mode. In some embodiments, an activation mechanism and/or a motion sensor can be used to turn the device on. In some embodiments, the device can be turned off by an activation mechanism and/or a motion sensor.

Figure 5:
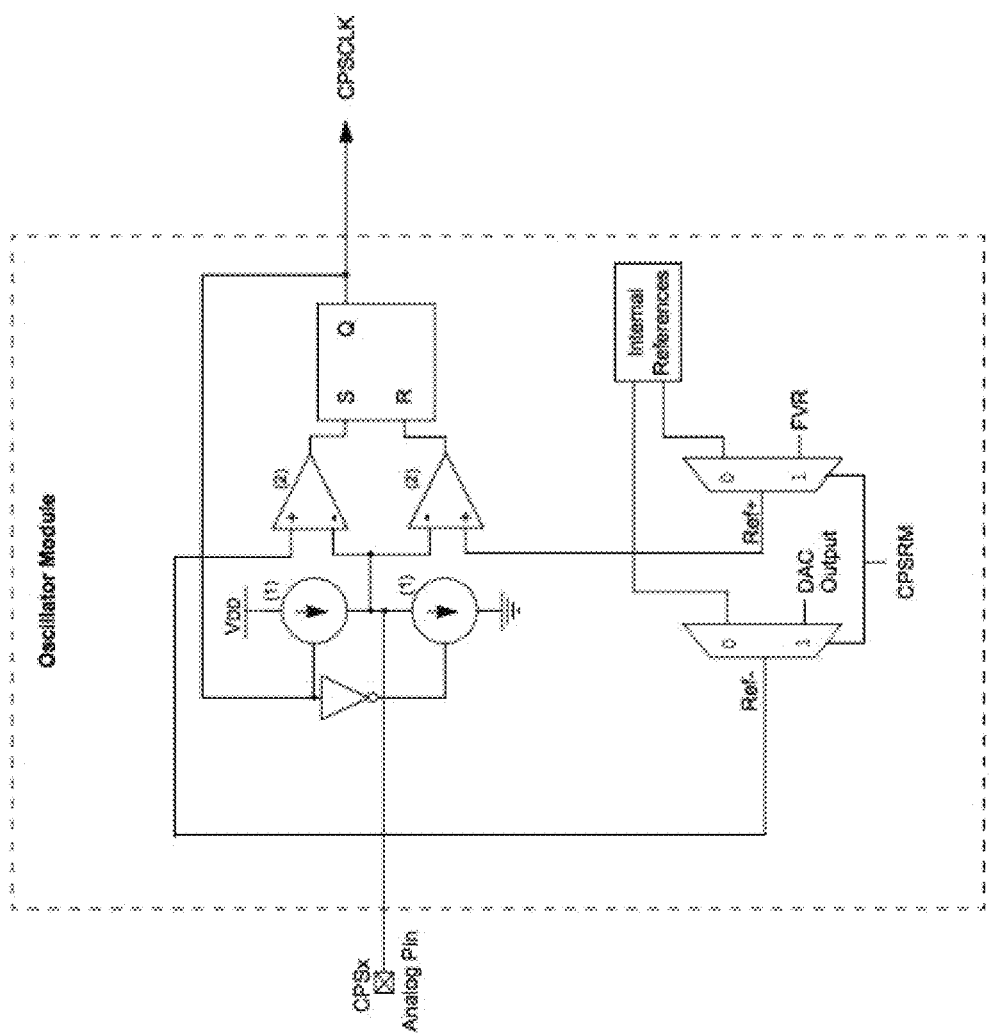
FIG. 5 shows an exemplary capacitive sense circuit.

The steps outlined in FIG. 4 can be carried out by microcontroller or other controller in or associated with the device. Exemplary circuitry for the steps outlined in FIG. 4 is shown in FIG. 5.

In some embodiments, the capacitive sensor can be a puff sensor, such as a capacitive membrane.

During use, it can be possible for the mouthpiece to trigger the capacitive sensor. As such, in some embodiments, the capacitance baseline can be reset (i.e., made higher) if the higher capacitance is detected to meet or be above the threshold capacitance for over a set period of time, such as 10 seconds.

In some embodiments, the lip sensor can be used to override a motion-based standby mode.

In some embodiments, more than one capacitive sensor can be used, for example, to help identify user skin touch vs lip touch. In some embodiments, a flow sensor and/or pressure sensor can be used in place of the capacitive lip sensor. In some embodiments, an inductive sensor can be used in place of the capacitive lip sensor.

Advantageously, the PID control loop and capacitive sensor control loops described herein can save power in the device, thereby conserving battery. The control loops can also ensure that plant matter and/or other vaporizable material is heated continuously at the desired temperature and/or vaporized only when the device is actively in use.

Any material that is capable of being aerosolized and inhaled by a user may be incorporated into a device described herein. For example, many materials have be contemplated for use with the present invention include, but are not limited to, those containing tobacco, natural or artificial flavorants, coffee grounds or coffee beans, mint, chamomile, lemon, honey, tea leaves, cocoa, and other non-tobacco alternatives based on other botanicals. The device can also be compatible for use with pharmaceutical compounds or synthetic compounds, either for pharmaceutical or pleasurable use. Any such compound which can be vaporized (or volatized) at a relatively low temperature and without harmful degradation products can be suitable for use with the device. Examples of compounds include, but are not limited to, menthol, caffeine, taurine, and nicotine.

As described herein, an electronic heater comprises a heater circuit, an oven and a printed circuit board to heat a vaporizable material to a generate an inhalable aerosol. The heater circuit may be flexible. In some embodiments, the flexible heater circuit is etched from a copper- or constantan-clad polyimide film. In some embodiments, a flexible heater is constructed by stamping (die-cutting) a thin sheet of constantan or copper. In this case, the heater circuit can be electrically insulated from adjacent conductive elements in the assembly, using polyimide or other suitable insulation that is stable at elevated temperatures. The heater circuit heats the attached oven, which then heats the cartridge or active substance by thermal conduction. The resistive heater circuit heats up as current passes through it. Heat is then conducted from the circuit to the oven walls. Thermal conduction continues from the oven walls into the cartridge or active substance. Heat can also transfer from the oven walls into the active substance or cartridge via convection and radiation.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaporizer device, comprising:
    a reservoir configured to hold a vaporizable material;
    a heater configured to heat the vaporizable material;
    a mouthpiece in communication with the reservoir;
    a sensor configured to output a plurality of sensor readings; and
    a controller configured to:
        detect use of the vaporizer device by a user via the sensor, wherein the detected use comprises contact with the mouthpiece; and
        regulate a temperature of the heater to a preselected temperature by at least applying a temperature control loop having inputs including at least one of the plurality of sensor readings, wherein the temperature control loop comprises a proportional integral derivative control algorithm.

2. The vaporizer device of claim 1, wherein the temperature control loop further includes as inputs at least the temperature of the heater and the preselected temperature.

3. The vaporizer device of claim 1, wherein the controller is further configured to:
    reduce the temperature of the heater by a first predetermined step amount when no contact with the mouthpiece is detected for greater than a first idle period; and
    reduce the temperature of the heater again by the first predetermined step amount when no contact is detected for a continuing idle period in addition to the first idle period.

4. The vaporizer device of claim 1, wherein the preselected temperature is selected from a plurality of predetermined temperature settings.

5. The vaporizer device of claim 1, wherein the use of the vaporizer device is detected based on the plurality of sensor readings meeting a threshold reading.

6. The vaporizer device of claim 1, wherein the controller is further configured to:
    determine a baseline sensor reading based on the plurality of sensor readings, the baseline sensor reading having a baseline value;
    determine a value based on a difference between a first sensor reading of the plurality of sensor readings and the baseline value; and
    adjust the temperature of the heater based on a difference between the value and a threshold.

7. The vaporizer device of claim 6, wherein the controller is further configured to determine the baseline value based on filtering the plurality of sensor readings.

8. The vaporizer device of claim 6, wherein the controller is further configured to calculate a percentage difference between the first sensor reading and the baseline value.

9. The vaporizer device of claim 6, wherein the controller is further configured to increase the temperature of the heater based on the value being at or above the threshold.

10. The vaporizer device of claim 6, wherein the threshold comprises an indication of a 0.5% change between the first capacitance reading and the baseline capacitance.

11. The vaporizer device of claim 6, wherein the controller is further configured to increase the temperature of the heater to an override temperature for a boost time period, when a difference between a first sensor reading of the plurality of sensor readings and a baseline sensor reading meets a threshold value.

12. A method, comprising:
    detecting, via a sensor coupled to a vaporizer device, use of the vaporizer device by a user, the use comprising contact with a mouthpiece of the vaporizer device, the vaporizer device comprising:
        a reservoir configured to hold a vaporizable material;
        a heater configured to heat the vaporizable material;
        the mouthpiece in communication with the reservoir;
        the sensor configured to output a plurality of sensor readings; and
    regulating a temperature of the heater to a preselected temperature by at least applying a temperature control loop having inputs including at least one of the plurality of sensor readings, wherein the temperature control loop comprises a proportional integral derivative control algorithm.

13. The method of claim 12, wherein the temperature control loop further includes as inputs at least the temperature of the heater and the preselected temperature.

14. The method of claim 12, further comprising decreasing the temperature of the heater below the preselected temperature based at least on the plurality of sensor readings.

15. The method of claim 12, further comprising increasing the temperature of the heater over the preselected temperature based at least on the plurality of sensor readings.

16. The method of claim 12, further comprising:
reducing the temperature of the heater by a first predetermined step amount when no contact with the mouthpiece is detected for greater than a first idle period; and
reducing the temperature of the heater again by the first predetermined step amount when no contact is detected for a continuing idle period in addition to the first idle period.

17. The method of claim 12, wherein the preselected temperature is selected from a plurality of predetermined temperature settings.

18. The method of claim 12, wherein the use of the vaporizer device is detected based on the plurality of sensor readings meeting a threshold reading.

* * * * *